(12) United States Patent
Chapman

(10) Patent No.: US 10,820,833 B2
(45) Date of Patent: Nov. 3, 2020

(54) CAPNOGRAPH SYSTEM FURTHER DETECTING SPONTANEOUS PATIENT BREATHS

(71) Applicant: Physio-Control, Inc., Redmond, WA (US)

(72) Inventor: Fred William Chapman, Newcastle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 360 days.

(21) Appl. No.: 15/836,658

(22) Filed: Dec. 8, 2017

(65) Prior Publication Data

US 2018/0160939 A1 Jun. 14, 2018

Related U.S. Application Data

(60) Provisional application No. 62/432,535, filed on Dec. 9, 2016.

(51) Int. Cl.
*A61B 5/083* (2006.01)
*A61M 16/00* (2006.01)
(Continued)

(52) U.S. Cl.
CPC ............ *A61B 5/0836* (2013.01); *A61B 5/087* (2013.01); *A61M 16/0003* (2014.02); *A61M 16/0051* (2013.01); *A61M 16/201* (2014.02); *A61N 1/39* (2013.01); *A61N 1/3925* (2013.01); *A61M 16/0048* (2013.01); *A61M 16/04* (2013.01); *A61M 16/085* (2014.02); *A61M 16/208* (2013.01); *A61M 2016/0015* (2013.01); *A61M 2016/0027* (2013.01); *A61M 2205/05* (2013.01);
(Continued)

(58) Field of Classification Search
CPC ....... A61B 5/0836; A61B 5/097; A61B 5/082; A61B 5/742; A61M 16/0003; A61M 16/085; A61M 16/0057; A61M 16/0051; A61M 16/04; A61M 16/0463; A61M 16/06; A61M 2205/583; A61M 2205/18; A61M 2205/3553; A61M 2205/3561; A61M 2016/102; A61M 2016/103; A61M 2016/0027
USPC .......... 73/720, 721, 726, 727; 600/532, 538, 600/543
See application file for complete search history.

(56) References Cited

U.S. PATENT DOCUMENTS 3,604,415 A 9/1971 Hoenig
3,762,408 A 10/1973 Cox et al.
(Continued)

*Primary Examiner* — Justine R Yu
*Assistant Examiner* — Kelsey E Baller
(74) *Attorney, Agent, or Firm* — Miller Nash Graham and Dunn

(57) ABSTRACT

A capnograph system may be used together with a ventilation system for a patient. The capnograph system may include a capnography module with a carbon dioxide detector, which may generate a carbon dioxide signal responsive to an amount of carbon dioxide detected within an air path of the ventilation system. A monitoring circuit may further detect a pressure within the air path. A processing component within the capnography module may generate a pressure signal responsive to the pressure detected in the air path. The pressure signal, alone or in combination with other signals such as the carbon dioxide signal, may be used to detect spontaneous breaths of the patient.

28 Claims, 12 Drawing Sheets

(51) Int. Cl.
*A61N 1/39* (2006.01)
*A61B 5/087* (2006.01)
*A61M 16/08* (2006.01)
*A61M 16/04* (2006.01)
*A61M 16/20* (2006.01)

(52) U.S. Cl.
CPC . *A61M 2205/18* (2013.01); *A61M 2205/3576* (2013.01); *A61M 2205/502* (2013.01); *A61M 2205/581* (2013.01); *A61M 2205/583* (2013.01); *A61M 2230/432* (2013.01)

(56) References Cited

U.S. PATENT DOCUMENTS

| | | | |
|---|---|---|---|
| 3,916,889 A | 11/1975 | Russell | |
| 4,003,377 A | 1/1977 | Dahl | |
| 4,164,219 A | 8/1979 | Bird | |
| 4,316,458 A | 2/1982 | Hammerton-Fraser | |
| 4,747,403 A * | 5/1988 | Gluck | A61M 16/0096 |
| | | | 128/204.21 |
| 4,915,103 A | 4/1990 | Visveshwara et al. | |
| 5,222,491 A | 6/1993 | Thomas | |
| 5,239,994 A * | 8/1993 | Atkins | A61M 16/0096 |
| | | | 128/204.18 |
| 5,376,044 A | 12/1994 | Tippin et al. | |
| 5,386,833 A * | 2/1995 | Uhen | A61B 5/0836 |
| | | | 600/532 |
| 5,551,420 A | 9/1996 | Lurie et al. | |
| 5,692,498 A | 12/1997 | Lurie et al. | |
| 6,155,257 A * | 12/2000 | Lurie | A61H 31/005 |
| | | | 128/204.18 |
| 6,634,357 B1 * | 10/2003 | Hamilton | A61M 16/20 |
| | | | 128/204.26 |
| 7,422,015 B2 | 12/2008 | Delisle et al. | |
| 7,530,353 B2 * | 5/2009 | Choncholas | A61M 16/085 |
| | | | 128/204.18 |
| 7,533,670 B1 | 5/2009 | Freitag et al. | |
| 7,841,988 B2 * | 11/2010 | Yamamori | A61B 5/0836 |
| | | | 128/204.23 |
| 8,728,001 B2 | 5/2014 | Lynn | |
| 9,173,595 B2 * | 11/2015 | Bohm | A61B 5/085 |
| 9,974,916 B2 * | 5/2018 | Scampoli | A61M 16/0808 |
| 2002/0033175 A1 | 3/2002 | Bateman et al. | |
| 2008/0139107 A1 | 6/2008 | Takeda et al. | |
| 2009/0151726 A1 | 6/2009 | Freitag | |
| 2012/0240932 A1 * | 9/2012 | Gusky | A61M 16/026 |
| | | | 128/204.21 |
| 2013/0006134 A1 * | 1/2013 | Doyle | A61B 5/0836 |
| | | | 600/532 |
| 2014/0066800 A1 * | 3/2014 | Takatori | A61B 5/0826 |
| | | | 600/532 |
| 2014/0180138 A1 * | 6/2014 | Freeman | A61N 1/3925 |
| | | | 600/484 |
| 2014/0326048 A1 * | 11/2014 | Jaffe | A61B 5/082 |
| | | | 73/31.05 |
| 2015/0153244 A1 * | 6/2015 | Nienhoff | F01N 3/208 |
| | | | 73/40 |
| 2015/0328417 A1 * | 11/2015 | Loser | A61M 16/024 |
| | | | 128/204.23 |
| 2016/0158472 A1 | 6/2016 | Wik | |
| 2016/0206839 A1 * | 7/2016 | Freeman | A61M 16/0003 |
| 2017/0325716 A1 * | 11/2017 | Coleman | A61B 5/087 |
| 2017/0368294 A1 * | 12/2017 | Orr | A61M 16/1005 |

* cited by examiner

FIG. 13 — METHODS

CAPNOGRAPH SYSTEM FURTHER DETECTING SPONTANEOUS PATIENT BREATHS

CROSS REFERENCE TO RELATED PATENT APPLICATIONS

This patent application claims priority from U.S. Provisional Patent Application Ser. No. 62/432,535, filed on Dec. 9, 2016.

BACKGROUND

Cardio Pulmonary Resuscitation (CPR) includes chest compressions and ventilations. Ventilations are artificial breaths that a rescuer, such as a paramedic, may inject into a patient's lungs, whether by using a ventilator system for administering breaths mechanically and artificially or not.

Some ventilator systems include an airway tube that is inserted into the patient's airway. Such an airway tube can be an endotracheal (ET) tube or a supraglottic airway laryngopharyngeal tube. The airway tube can be inserted from an airway opening of the patient, which may be the mouth, the nostrils, a small incision in the trachea, etc. The insertion is a process that is known as intubation, and is often performed according to a process called Rapid Sequence Intubation (RSI). When intubation is thus complete, the artificial breaths can be delivered at a certain appropriate and prescribed rate.

A patient might have a reflexive reaction against the intubation. To prevent that, a rescuer may first need to administer sedation and/or a paralytic drug, and then wait for it to take effect. In the event that the patient is unconscious, for example from a cardiac arrest, the drugs may not be needed. Still, a patient in cardiac arrest can be intubated during arrest or shortly after return of spontaneous ventilation, and ventilation at the certain prescribed rate is still needed in those patients.

Problems may arise when the sedation and/or the paralytic drug start wearing off. It can be worse when both have been administered, and they start wearing off at different times. A patient may attempt one or more spontaneous breaths, which can be a good indication that mechanical ventilation is no longer necessary, or that the breaths being administered mechanically do not provide enough ventilation.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor. This approach in and of itself may also be inventive.

BRIEF SUMMARY

The present description gives instances of medical devices, systems, components, and methods, the use of which may help overcome problems and limitations of the prior art. In embodiments, ventilation systems may be used for patients, and spontaneous breaths of patients may be detected that have cardiac arrest, had cardiac arrest, or for any reason had been intubated with an endotracheal tube to protect their airway and/or enable mechanical ventilation.

In embodiments, a capnograph system may be used together with a ventilation system for a patient. The capnograph system may include a capnography module with a carbon dioxide detector, which may generate a carbon dioxide signal responsive to an amount of carbon dioxide detected within an air path of the ventilation system. A monitoring circuit may further detect a pressure within the air path. A processing component within the capnography module may generate a pressure signal responsive to the pressure detected in the air path. The pressure signal, alone or in combination with other signals such as the carbon dioxide signal, may be used to detect spontaneous breaths of the patient.

In embodiments, a monitor system may detect spontaneous breaths by a patient. In particular, the monitor system may be used together with a ventilation system that includes an airway adapter. In some embodiments, the monitor system includes a defibrillator module, in which case it is a monitor-defibrillator. The monitor system may include a capnography module with a carbon dioxide detector, which may generate a carbon dioxide signal responsive to an amount of carbon dioxide detected within an air path of the ventilation system. The capnography module may also include a pressure detector to detect a pressure within the air path, and a processing component to generate a pressure signal from the detected pressure. A processor may detect a spontaneous breath of the patient from an aspect of the pressure signal, and possibly also from an aspect of the carbon dioxide signal.

In embodiments, a capnograph airway adapter for a ventilator has a side tube adapted to further detect spontaneous patient breaths. In particular, the capnograph airway adapter can be configured to be used together with a ventilation system that includes a gas source and an airway tube. The capnograph airway adapter may include an airway adapter configured to be coupled between the gas source and the airway tube, and a side tube configured to be coupled with the capnograph airway adapter. A strain is gauge coupled to the side tube, and is configured to be coupled with a bridge circuit for generating a pressure signal about a pressure in the side tube.

In embodiments, a capnograph airway adapter for a ventilator is adapted to further detect spontaneous patient breaths. In particular, the capnograph airway adapter can be configured to be used together with a ventilation system that includes a gas source and an airway tube. The capnograph airway adapter may include an airway adapter configured to be coupled between the gas source and the airway tube. A strain gauge can be coupled to the airway adapter, and be configured to be coupled with a bridge circuit for generating a pressure signal about a pressure in the airway adapter.

In embodiments, an impedance threshold device (ITD) is adapted to help detect spontaneous patient breaths. In particular, the impedance threshold device can be used together with a ventilation system that includes a gas source and an airway tube. The impedance threshold device includes a tube section that can be coupled between the gas source and the airway tube, and an inflow valve within the tube section. The inflow valve can be closed so as to block the air path until a negative airway pressure threshold is exceeded, at which time the closed inflow valve can open so as to unblock the blocked air path. A strain gauge is coupled to the tube section, and is configured to be coupled with a bridge circuit for generating a pressure signal about a pressure in the tube section.

In embodiments, an impedance threshold device (ITD) is adapted to help detect patient carbon dioxide. In particular, the impedance threshold device can be used together with and a capnography module and a ventilation system that includes a gas source and an airway tube. The impedance threshold device includes a tube section that can be coupled between the gas source and the airway tube, and a side tube configured to be coupled to the capnography module. An inflow valve within the tube section can be closed so as to block the air path until a negative airway pressure threshold is exceeded, at which time the closed inflow valve can open so as to unblock the blocked air path.

In embodiments, a ventilator endotracheal tube has a strain gauge for helping detect spontaneous patient breaths. In particular, an endotracheal (ET) system for a ventilator includes an ET tube, and a strain gauge coupled to the ET tube. A bridge circuit can be configured to be coupled with the strain gauge so as to detect pressure changes within the ET tube.

An advantage can be that the detected spontaneous breaths can be communicated to rescuers, who can adjust accordingly what they do. In some embodiments, spontaneous breaths can be detected without having a sensor in an air path, and inexpensively in many embodiments. In addition, the performance of a rescue team can be assessed more accurately. For example, spontaneous breaths will not surreptitiously blemish the record of a team member who has been ventilating at a proper pace.

Moreover, the detected spontaneous breaths can become part of the overall resuscitation record. Presence or absence of patient-initiated breaths can give clues about respiratory drive of patients, which is related to adequacy of ventilation. It can also give clues about the status of paralytic drugs administered as part of Rapid Sequence Intubation (RSI). That is, documentation can be created as to when a paralytic drug has worn off.

These and other features and advantages of the claimed invention will become more readily apparent in view of the embodiments described and illustrated in this specification, namely from this written specification and the associated drawings.

DETAILED DESCRIPTION

As has been mentioned, the present description is about medical devices, systems, components and methods. Embodiments are now described in more detail.

Figure 1:
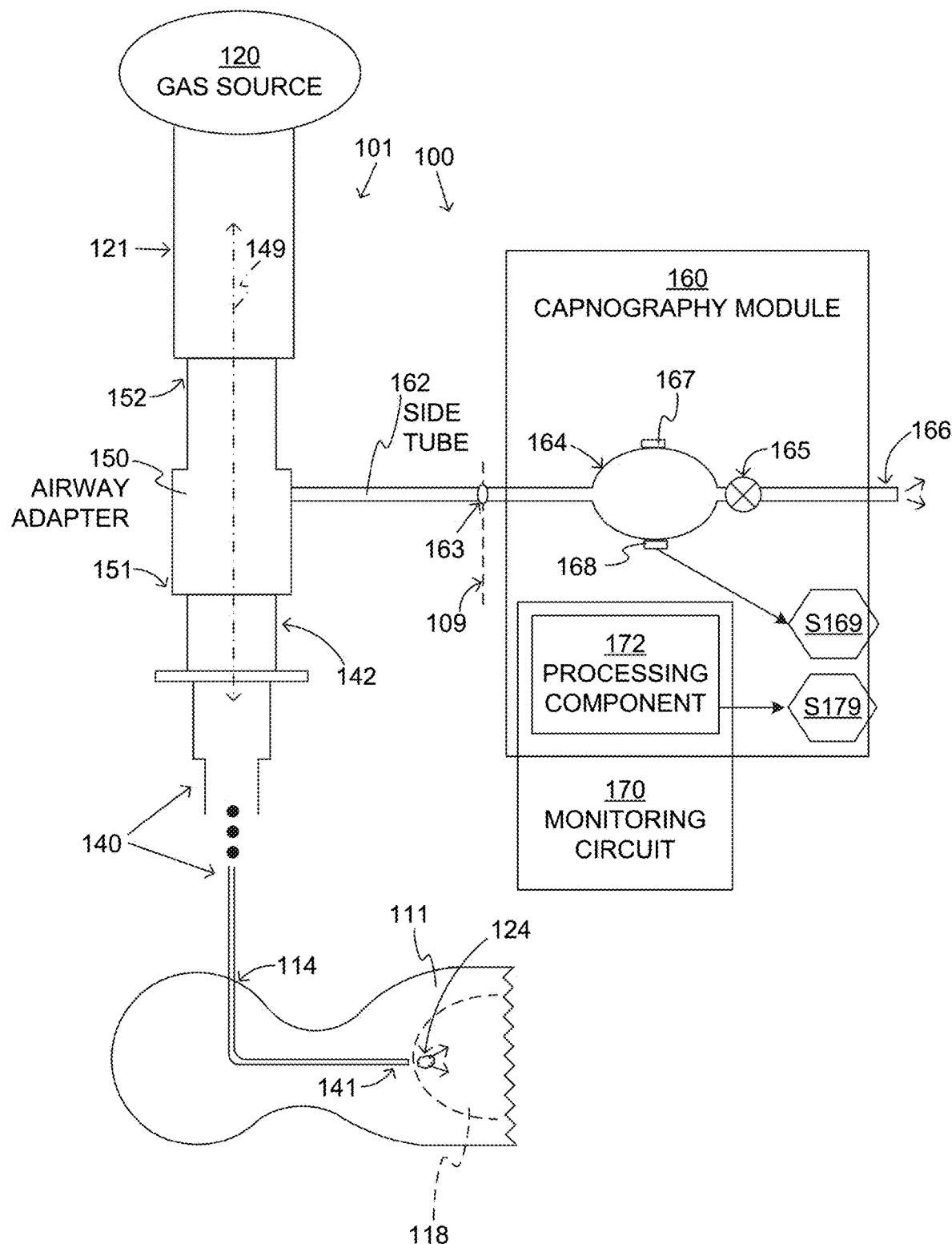
FIG. 1 is a diagram of sample components of a capnograph system and of a ventilation system made according to embodiments.

FIG. 1 shows a portion of a patient 111, with an airway opening 114 and one of their lungs indicated as 118. A capnograph system 100 according to embodiments is shown, which is configured to be used together with a ventilation system 101 according to embodiments. In some embodiments, the components of system 100 and system 101 may overlap, for better cooperation.

Ventilation system 101 includes a gas source 120. The gas of source 120 can be oxygen, air, a mixture thereof, other combinations of gases, etc. Gas source 120 can be configured to expel repeated bursts of the gas through a gas source tube 121. For expelling, gas source 120 may be mechanized or manual. In some manual embodiments, gas source 120 includes a bag that can be squeezed by a rescuer, each squeezing delivering one of the bursts.

Ventilation system 101 may have additional components, which are not shown so as not to clutter FIG. 1. For example, a 1-way valve can be added some place after gas source 120. Such a 1-way valve performs two functions. First, when an artificial breath is administered, it allows gas from gas source 120 to pass into air path 149, and from there eventually to lung 118 of patient 111. Second, when patient 111 exhales, in other words, expires, the 1-way valve blocks the expired gases from reaching back to gas source 120; rather, the 1-way valve redirects these expired gases to be exhausted in the environment, or another tube instead.

A ventilation system according to embodiments includes and/or is configured to work with an airway tube. Examples of airway tubes include an endotracheal (ET) tubes, supraglottic airway laryngopharyngeal tubes, etc. In this description often an ET tube is shown, but that is by way of example and not of limitation, plus aspects of its description for purposes of this document may apply also to other types of airway tubes.

Ventilation system 101 also includes an endotracheal (ET) tube 140, of which two portions are shown in different scales, and connected by three dots. In particular, patient 111 is intubated by ET tube 140, and a first portion of ET tube 140 has been inserted through airway opening 114 into the trachea of patient 111. As such, a first end 141 of ET tube 114 is thus brought close to lung 118. A second portion of ET tube 140 is also shown, having a second end 142.

ET tube 140 defines an air path 149 that communicates with gas source tube 121 and gas source 120. As such, when ET tube 140 is thus inserted in the patient's airway, it can be configured so as to guide the bursts 124 of gas as artificial inhalations to lung 118 of patient 111. Gas expulsion by source 120 results in a pressure difference between the interior of ET tube 140 and the atmosphere, slightly stretching ET tube 140. The pressure in the interior of ET tube 140 is referred to as the patient's airway pressure and is also closely related to the patient's intrathoracic pressure.

Additional components may be coupled between ET tube 140 and gas source 120, in a manner that preserves and accommodates air path 149. Such components may include adapters, fittings, valves, etc. Coupling can happen because the components are usually tubular, and circular, and employ a male-female matching configuration.

In the example of FIG. 1 such a component is an airway adapter 150, which is configured to be coupled between gas source 120 and ET tube 140. Airway adapter 150 has a first end 151 that is coupled to second end 142 of ET tube 140. Airway adapter 150 also has a second end 152 that is coupled to gas source tube 121. Airway adapter 150 has a hollow interior, so as to accommodate air path 149 when it is thus coupled.

Capnograph system 100 can be configured to detect carbon dioxide in exhalations of patient 111, and also a pressure in air path 149. Capnograph system 100 may include a capnography module 160 that has a carbon dioxide detector 168. Carbon dioxide detector 168 can be configured to generate a carbon dioxide signal S169 responsive to an amount of carbon dioxide detected within air path 149 of ventilation system 101.

Capnograph system 100 may also include a monitoring circuit 170 that is distinct from carbon dioxide detector 168. Monitoring circuit 170 can be configured to detect a pressure in air path 149. Monitoring circuit 170 may have a processing component 172 within capnography module 160, and distinct from carbon dioxide detector 168. In fact, in some embodiments, monitoring circuit 170 is wholly included within capnography module 160, while in other embodiments not necessarily. Processing component 172 can be configured to generate a pressure signal S179 responsive to the pressure detected in air path 149 by the monitoring circuit 170. As explained later in this document, pressure signal S179, alone or in combination with other signals such as carbon dioxide signal S169, may be used to detect spontaneous breaths of the patient.

In embodiments, capnography module 160 communicates with air path 149 by means of a side tube 162, which can be configured to be coupled between airway adapter 150 and capnography module 160. In fact, airway adapter 150 may be interposed in air path 149 for the purpose of providing the opportunity of side tube 162 to access air path 149, for sampling the gases and the pressure therein. The gases include a mixture of gases expelled by source 120 as bursts, and also from patient 111 as exhalations. For operation, side tube 162 may be passed through an opening 163 in a housing 109 of capnography module 160, or of a monitor that houses capnography module 160, a monitor-defibrillator system, etc. In such configurations, capnography module 160 can be characterized as a side stream capnograph.

In some embodiments, capnography module 160 includes a cuvette 164, which is a small chamber. Side tube 162 can be coupled to cuvette 164. Capnography module 160 may also include a pump 165, which is configured to draw gas from air path 149 into cuvette 164. This way, gases in air path 149 can be sampled while in cuvette 164. After that, the sampled gases can be disposed of via an exhaust tube 166. It will be understood that pump 165 withdraws, for sampling the vertical column of air path 149, relatively little gas compared to what is needed for ventilating the patient. In addition, as long as pump 165 withdraws gas at a constant rate, that will not mask the transient nature of a peak that is intended to be detected.

In such embodiments, a light source 167 in capnography module 160 may illuminate the interior of cuvette 164, and carbon dioxide detector 168 detects an amount of the carbon dioxide within cuvette 164, by measuring how much light from source 167 reaches it. In some embodiments, light source 167 emits infrared (IR) light.

As mentioned above, pressure signal S179, alone or in combination with other signals such as carbon dioxide signal S169, may be used by a processor to detect spontaneous breaths of the patient according to embodiments. Examples are now described.

Figure 2:
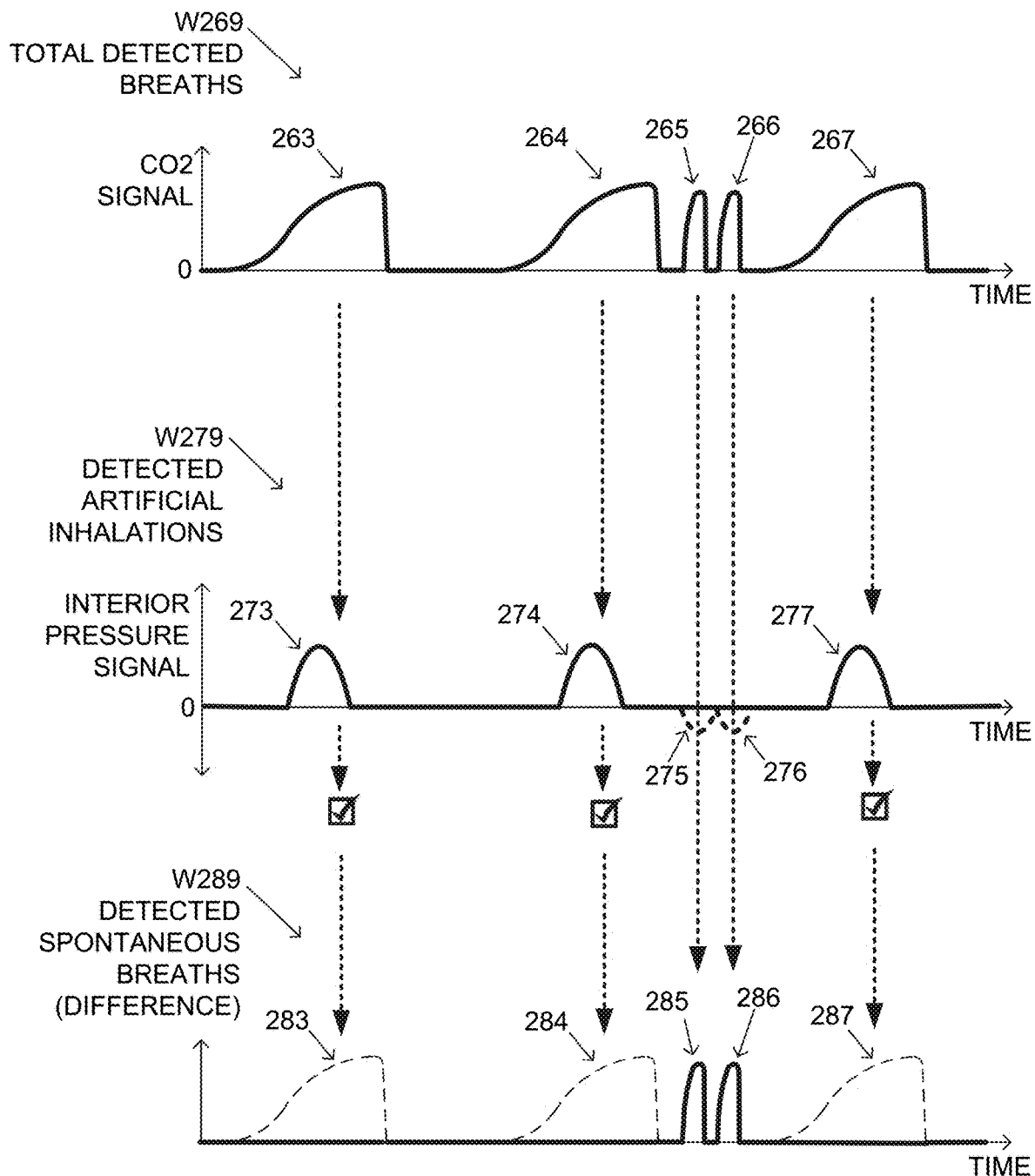
FIG. 2 illustrates a sample comparison of sample time diagrams of waveforms of signals of FIG. 1, for detecting spontaneous patient breaths according to embodiments.

FIG. 2 illustrates a sample comparison of sample time diagrams of waveforms W269, W279. Waveforms W269, W279 can be those of signals S169, S179 respectively. Aspects of waveforms W269, W279 are a baseline value, and peaks away from the baseline value. The baseline value can be set to zero, or be thought of as zero. The peaks are transient, in the sense that the waveforms return to the baseline value.

Waveform W269 indicates an amount of carbon dioxide. Strictly speaking, it is a measure of the partial pressure of carbon dioxide, of amount of carbon dioxide in cuvette 164, and so on.

Waveform W269 has peaks 263, 264, 265, 266, 267, which correspond to exhalations. These exhalations can be from both the artificial breaths and any spontaneous breaths.

Waveform W279 indicates pressure changes within air path 149, from a baseline. As will be appreciated, in cases where an ET tube forms an airtight seal, at a first approximation the pressure within air path 149 is uniform within air path 149, and even within side tube 162 and cuvette 164. This uniform pressure is shown as the baseline zero, even though it may have a non-zero value. It can be thought of as the difference between pressure in the airway and pressure in the ambient atmosphere surrounding the airway tube. At a second approximation, there can be pressure waves in advance of a new pressure being established, plus pump 165 may introduce a boundary condition of reducing pressure. Notwithstanding the effect of pump 165, pressures changes from the baseline within air path 149, i.e. changes from artificial breaths and from any spontaneous breaths, can result in corresponding pressure changes being established within side tube 162 and within cuvette 164.

Waveform W279 has positive peaks 273, 274, 277, plus negative peaks 275, 276 that are discussed later. Positive peaks 273, 274, 277 amount to gusts or bursts by gas source, in other words, artificial inhalations for the patient.

For detecting spontaneous breaths by the patient, waveform W289 is made first by repeating waveform W269, and then by removing from that waveform peaks that can be attributed to peaks of waveform W279. In other words, waveform W289 first is made with peaks 283, 284, 285, 286, 287, which repeat peaks respective 263, 264, 265, 266, 267 of waveform W269. But then, peaks 283, 284, 287 are removed from waveform W289, because their presence is explained, attributed to peaks 273, 274, 277 as artificial inhalations. Accordingly, waveform W289 is left only with peaks 285, 286, from peaks 265, 266, which can be deduced to be spontaneous breaths.

The description above used only positive pressure in waveform W279. That would be applicable, for example, if only increases of the pressure in the airway were detectable. In some embodiments, negative pressure changes can also be detected, which would result in peaks 275, 276. Negative pressure changes are sometimes called "negative pressure". Similarly, where pressure detectors are provided in this disclosure to detect pressure, it is often the change in pressure that is of interest for signal S169 to convey. In such embodiments, waveform W279 of pressure signal S179 alone can be used for detecting the presence of spontaneous breaths, since spontaneous breaths result in negative pressure changes. As such, in those embodiments a comparison with carbon dioxide waveform W269 may not be necessary, but used nevertheless to confirm the presence of corresponding exhalation peaks 265, 266, and so on. Of course, negative pressure peaks of much magnitude may be uncommon, except when an ITD is being used and a spontaneous inspiration is initiated.

A person skilled in the art will recognize that a simplification has been made in FIG. 2, for explaining more easily the correspondence, and attribution, of peaks in waveforms W269 and W279. The simplification is that corresponding peaks are shown as occurring at the same time. This might indeed be the case if all the sensing were happening at the same location within the vertical column of air path 149. Where, however, signal S169 is derived by a detection of gas withdrawn after side tube 162, waveform W269 may appear with a concomitant first time delay relative to FIG. 2. And, if the pressure is detected within the column of air path 149, waveform W279 may appear with no time delay. Or, if the pressure is detected on side tube 162 or in module 160, waveform W279 may appear with a concomitant second time delay relative to FIG. 2. The potentially first time delay may be different from the second time delay. For attribution of the peaks, the potentially different time delays can be corrected by a processor, whether in in real time, or by being known in advance. Knowing in advance can be by the factory, by a calibration process, and so on. For detection, detection windows may be established for confirming a peak is established or not. In addition, detection windows may be set to prevent negative peak detection, and so on.

Of course, in matching and interpreting aspects such as peaks for detecting spontaneous breaths, a person skilled in the art may use additional features. For example, a trailing edge of the $CO_2$ peaks in waveform W269 may occur when a fresh burst of gas enters the air path from the gas source, or even ambient air if permitted. If the airway pressure is positive at the time the $CO_2$ level drops to zero, this can be detected as an administered artificial breath; if, however, the airway pressure is not positive at the time the $CO_2$ level drops to zero, the breath must be a spontaneous breath drawn in by the patient. Moreover, the person skilled in the art will adjust for the impact of a 1-way valve; even where present, this impact may not be much, as its time constant may be slower than what is being detected.

Figure 3:
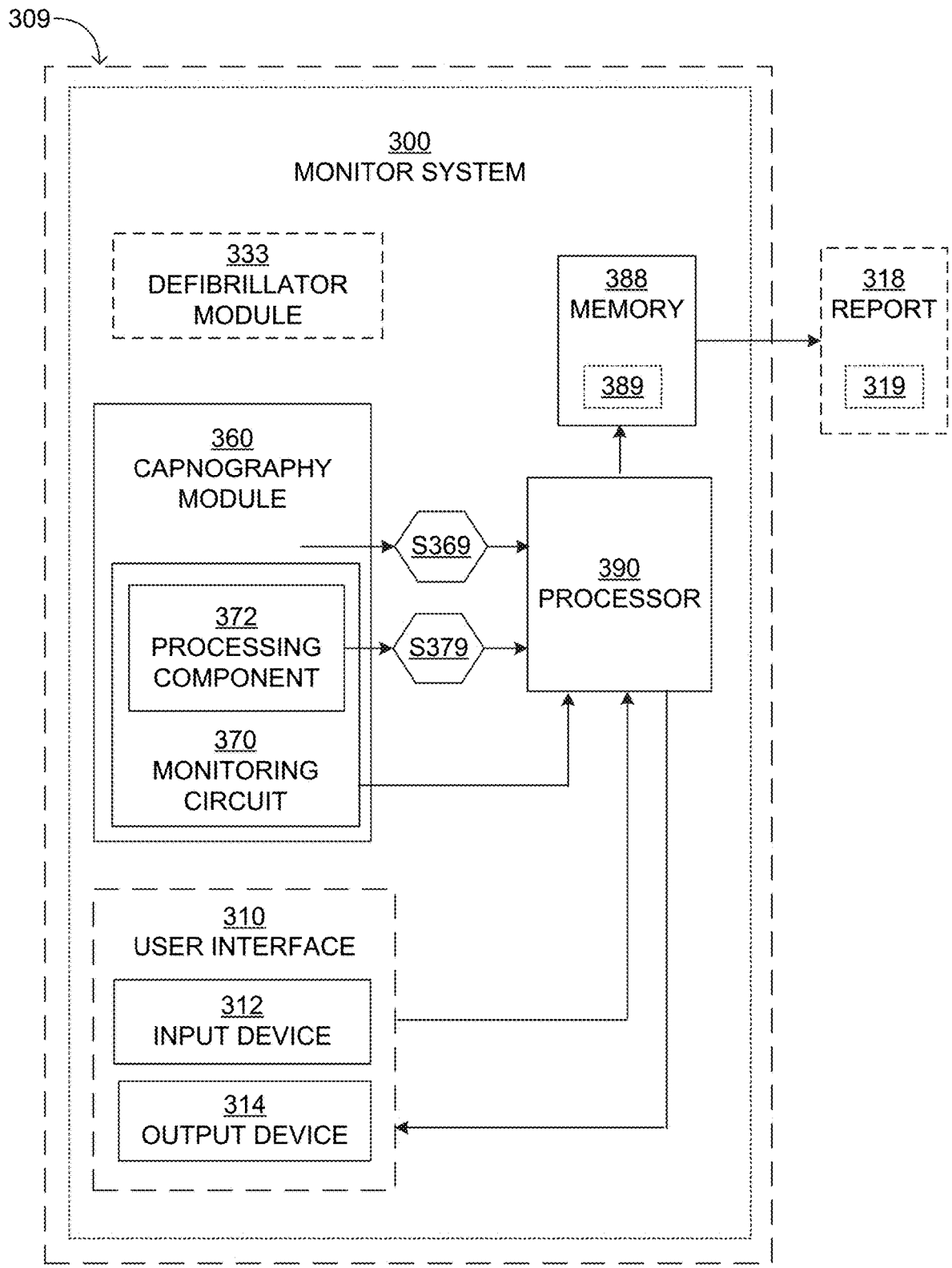
FIG. 3 is a diagram showing sample components of a monitor system that may include a capnography module of FIG. 1, according to embodiments.

Referring now to FIG. 3, in some embodiments, a monitor system 300 may detect spontaneous breaths by a patient. In particular, monitor system 300 may be used together with a ventilation system that includes an airway adapter, as seen in FIG. 1. Of course, embodiments of FIG. 1 can be implemented with or without monitor system 300. In other words, monitor 300 is optional, in the sense that what is described for using the pressure signal S179 may also take place within an overall monitor 300.

In some embodiments, monitor system 300 is provided in a housing 309. Monitor system 300 may include a defibrillator module 333, in which case system 300 is a monitor-defibrillator. Monitor system 300 may include a capnography module 360, which can be as described elsewhere in this document, and generate a carbon dioxide signal S369 similar to S169. Capnography module 360 may include a pressure detector (not shown in FIG. 3), to detect a pressure within the air path of the ventilation system.

In general, a monitoring circuit 370 may detect a pressure within the air path. Monitoring circuit 370 may include a processing component 372 similarly to what is described elsewhere in this document. Processing component 372 may generate a pressure signal S379 responsive to the pressure detected in the air path. In the embodiment of FIG. 3, monitoring circuit 370 is completely part of capnography module 360.

Monitor system 300 also includes a processor 390, which can be coupled to receive pressure signal S379, and optionally also carbon dioxide signal S369. Processor 390 may optionally be part of capnography module 360. Either way, processor 390 may detect a spontaneous breath of the patient from an aspect of pressure signal S379, and possibly also from an aspect of carbon dioxide signal S369. As also explained with reference to FIG. 2, processor 390 can be configured to detect the spontaneous breath from aspects, such as peaks, of pressure signal S379 and of carbon dioxide signal S369. In fact, detection can be from mismatched aspects of these signals.

As further explained with reference to FIG. 2, processor 390 can be configured to detect spontaneous breaths from an aspect of pressure signal S379 that indicates negative pressure. Such aspect can be negative changes in a baseline pressure signal, for example negative peaks 275, 276. In some embodiments, processor 390 is configured to confirm the detected spontaneous breath from an aspect of carbon dioxide signal S369, for example as described above for peaks 265, 266.

A capnograph system according to embodiments, and/or monitor system 300, may further include an output device 314. If monitor system 300 is indeed provided, output device 314 can be part of a user interface 310 of monitor 300. Output device 314 can be configured to output a human-perceptible indication, such as a sound, a light, a screen indication and the like, responsive to processor 390 receiving pressure signal S379. As such, output device 314 can include a light, a screen, a speaker, and so on. The human-perceptible indication can be that spontaneous breaths are indicated, and that the rescue team should consider reacting to them. Additional human-perceptible indications could be provided for additional events, for example responsive to the mechanical breaths. Such can be useful guidance to the person taking care of the patient. Moreover, items mentioned below for reporting may also be shown on a screen, such as reporting the number (or rate) of spontaneous and positive pressure breaths, and so on.

A capnograph system according to embodiments, and/or monitor system 300, may further include a memory 388. Memory 388 may optionally be part of capnography module 360. Memory 388 can be configured to store a record 389, responsive to processor 390 receiving pressure signal S379. As such, record 389 can indicate spontaneous breaths, of the type detected at waveform W289 of FIG. 2.

After an event, a report 318 can be generated. Report 318 may include, along with other events, a record 319 of spontaneous breaths that can be derived from record 389. Such other events may include efforts of the rescue team, shocks delivered by defibrillator module 333, and other data captured by monitoring circuit 370. There can be reporting separately the number (or rate) of spontaneous and positive pressure breaths, carbon dioxide ($CO_2$) levels (end tidal or maximum) separately for the spontaneous and positive pressure breaths. This might be useful in the future, while it is a good idea to have some real data gathered by such a system, to better define how a clinician should use those two different $CO_2$ levels.

Report 318 may further include data entered by the rescue team, for example what sedation and/or paralytic drugs were delivered and when. Such entries can be made by an input device 312 of user interface 310. As such, input device 312 can include a touchscreen, other haptic device, a keyboard, keypad, custom buttons, etc. Moreover, report 318 may include statistics extracted from the performance of the rescue team, for example a Figure of Merit about artificially delivered breaths, about reacting to the detected spontaneous breaths, etc.

Sample embodiments of capnograph systems are now described, for how monitoring circuit 170 of FIG. 1 can be implemented.

Figure 4:
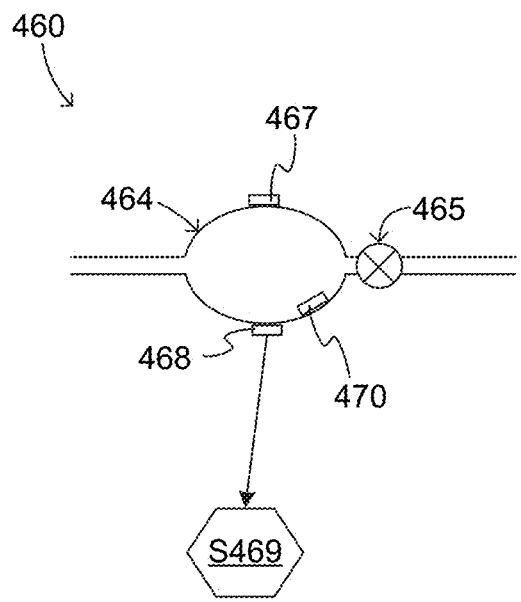
FIG. 4 is a diagram of a sample embodiment of a capnography module of FIG. 1.

Referring now to FIG. 4, in an embodiment 460, a cuvette 464 has gas drawn into it by a pump 465. A carbon dioxide detector 468, assisted by a light source 467, generates a carbon dioxide signal S469, all similarly to what was described above. In embodiment 460, the previously mentioned monitoring circuit includes a pressure sensor 470. Pressure sensor 470 can be configured to detect a pressure of the gas within cuvette 464, for example by being within cuvette 464. In other words, the pressure within the air path is detected by detecting pressure within cuvette 464.

Figure 5:
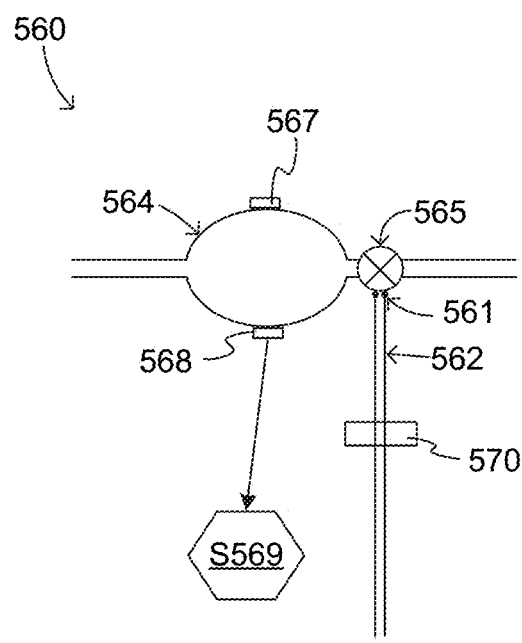
FIG. 5 is a diagram of another sample embodiment of a capnography module of FIG. 1.

For another example, referring now to FIG. 5, in an embodiment 560, a cuvette 564 has gas drawn into it by a pump 565. A carbon dioxide detector 568, assisted by a light source 567, generates a carbon dioxide signal S569, all similarly to what was described above. In embodiment 560, pump 565 includes at least one power node 561. Pump 565 can be configured to receive a pump driving signal at power node 561, and to operate as described above responsive to the pump driving signal. The pump driving signal can be electrical of course, and one or more conductors 562 may deliver the pump driving signal to power node 561.

In embodiment 560, the previously mentioned monitoring circuit may include a driving sensor 570 configured to detect changes in the pump driving signal. These changes in the pump driving signal can be because, when there are positive pressure events of artificial inhalations, pump 565 will need to work momentarily less hard to maintain the same rate of operation, and therefore momentarily draw less current. Plus, when there are negative pressure events of spontaneous breaths, pump 565 will need to work momentarily harder to maintain the same rate of operation, and therefore momentarily draw more current. As such, driving sensor 570 can be configured to detect voltage at power node 561, or current at one or more conductors 562, and so on.

Figure 6:
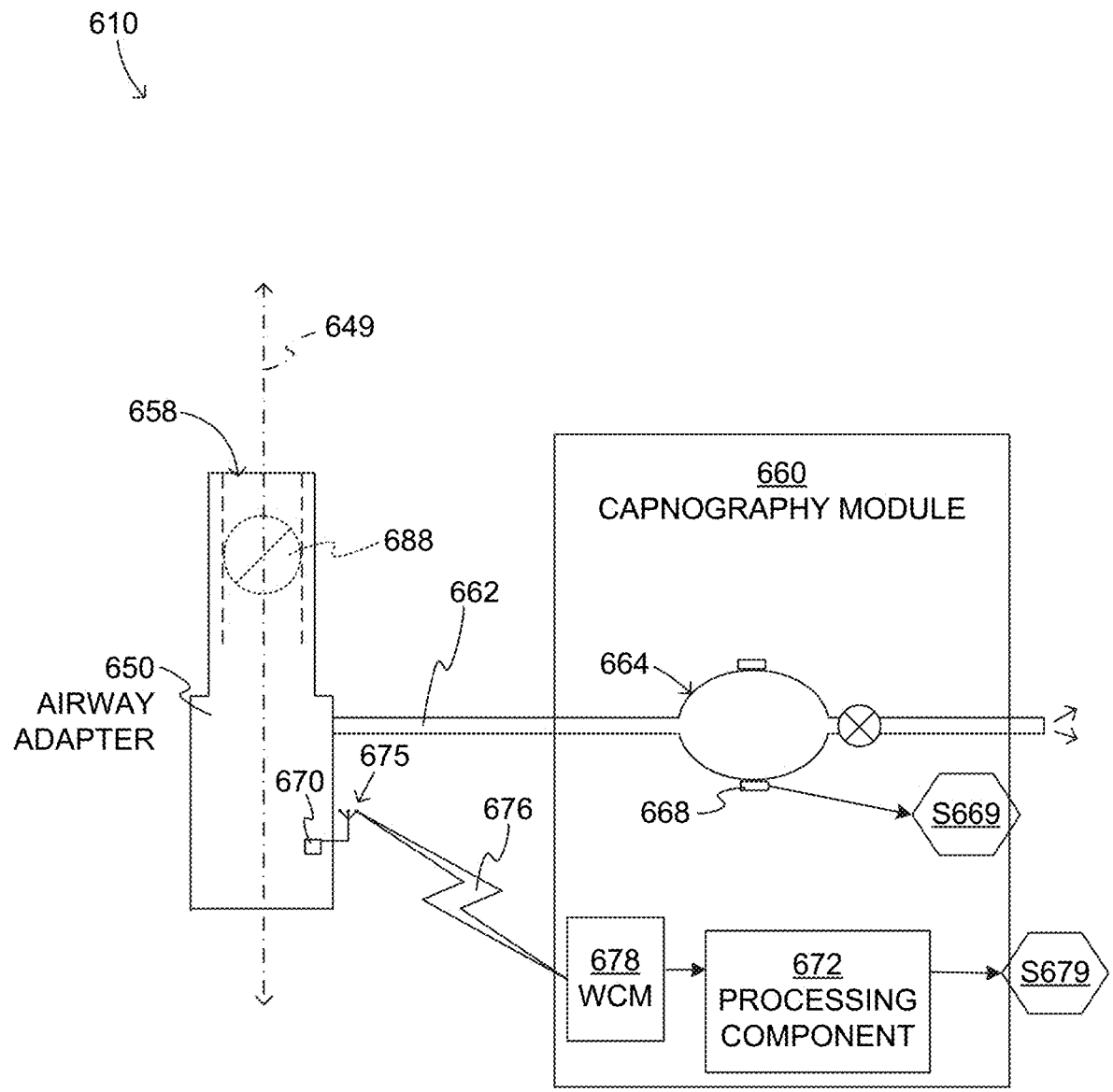
FIG. 6 is a diagram of sample embodiments of an airway adapter used together with an embodiment of a capnography module.

Referring now to FIG. 6, in an embodiment 610, an airway adapter 650 has a hollow interior 658 for accommodating an air path 649. Airway adapter 650 can communicate with a capnography module 660 via a side tube 662. Capnography module 660 includes a cuvette 664. Moreover, a carbon dioxide detector 668 can generate a carbon dioxide signal S669 about a gas in cuvette 464, all similarly to what was described above. In addition, capnography module 660 includes a processing component 672.

In embodiment 610, the previously mentioned monitoring circuit includes a pressure detector 670. Pressure detector 670 can be coupled to airway adapter 650, and configured to detect a pressure in hollow interior 658. Pressure detector 670 can be configured to generate a pressure detection signal responsive to the pressure detected in hollow interior 658. Moreover, the monitoring circuit may further include an antenna 675. Antenna 675 can be configured to transmit wirelessly the pressure detection signal.

In embodiment 610, capnography module 660 also includes a wireless communication module (WCM) 678. WCM 678 can be configured to receive the wirelessly transmitted pressure detection signal, for example over a communication link 676. This wireless communication link 676 can be implemented in a number of ways. For example, antenna 675 can be the antenna of a Radio Frequency Identification (RFID) tag on which values of the pressure detection signal are written, and WCM 678 can include an RFID reader that queries the RFID tag frequently enough to detect changes.

A related suitable device is Pressure and Temperature Sensor, Ultra-Miniature, High-Temperature, Low Frequency (134 KHz) RFID Passive Wireless Sensor which, at the time this document was initially filed with the U.S. Patent Office, was offered by PHASE IV ENGINEERING, INC., 2820 Wilderness Place Unit C, Boulder, Colo. 80301.

WCM 678 can be further configured to convey an interim signal to processing component 672, responsive to the received pressure detection signal. In embodiment 610, processing component 672 can be configured to generate a pressure signal S679 responsive to the received interim signal.

In some embodiments an inflow valve is further provided within the interior of the airway adapter, for increasing the duration and magnitude of negative airway pressures. This type of inflow valve is also known as CPR inflow valve and impedance threshold device (ITD) and can be made, for example, as described in U.S. Pat. No. 5,692,498. Such a CPR inflow valve may promote venous blood flow into the heart and lungs from the peripheral venous vasculature, especially during CPR. It should be noted, however that, where such an inflow valve is provided, perhaps care should be taken to account for a strain gauge being also used, and being subjected to negative air path pressure. In particular, if a patient initially tries to take a breath against resistance of the inflow valve, a tube section or adapter may contract. This should be considered in terms of the scenario, in particular whether the patient will be expected to be taking breaths voluntarily, etc.

For example, in embodiment 610 an inflow valve 688 is optionally provided within interior 658 of airway adapter 650. Inflow valve 688 can be configured to be closed so as to block air path 649 and thus prevent the bursts of gas from entering the lungs until a negative airway pressure threshold is met or exceeded. This negative airway pressure threshold can be set by how the valve is made, or be adjustable, in the field or by a medical director. At the time that the threshold is met or exceeded, the then-closed inflow valve 688 can be configured to open, so as to unblock the then-blocked air path 649.

These embodiments of FIG. 6 contemplate putting components within air path 649. Over time, matter may accumulate onto such components, which can create problems such as varying the measurements and even getting in the way of effective ventilation. As such, cleaning and maintenance may be needed.

There is a number of ways to detect pressure within the air path and, more particularly, changes in that pressure, according to embodiments. Since transients are of interest, measurement need not be very accurate and the pressure signal need not be high fidelity. For example, sensors could include capacitive sensing of the presence of positive airway pressure. Additional examples are now described.

In some embodiments, the previously mentioned monitoring circuit includes a strain gauge, and a bridge circuit configured to be coupled electrically with the strain gauge. The strain gauge may indicate when an elastic component changes size due to pressure inside it; for example, a component's circumferential size may become larger if there is a positive pressure change from the baseline, or smaller if there is a negative pressure from the baseline. The bridge circuit can be used to detect a change in the electrical resistance of the strain gauge. The bridge circuit may or may not be within the capnography module. The bridge circuit may or may not part of the previously mentioned processing component. Examples are now described.

Figure 7:
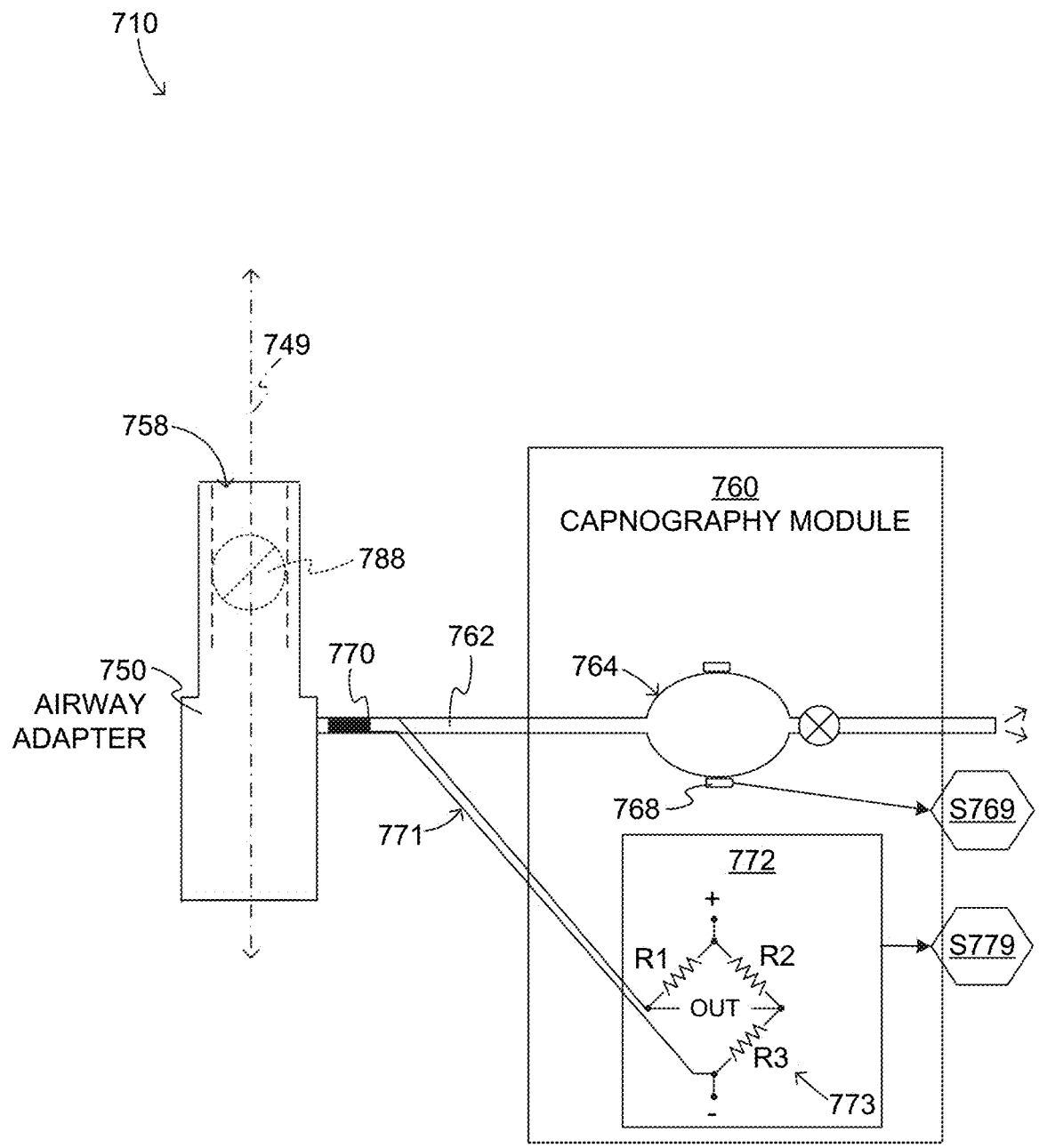
FIG. 7 is a diagram of sample embodiments of an airway adapter used together with a side tube with a strain gauge and a capnography module.

Referring now to FIG. 7, in an embodiment 710, an airway adapter 750 has a hollow interior 758 for accommodating an air path 749. A CPR inflow valve 788 can optionally be provided within interior 758 of airway adapter 750. Airway adapter 750 can communicate with a capnography module 760 via a side tube 762. Capnography module 760 includes a cuvette 764. Moreover, a carbon dioxide detector 768 can generate a carbon dioxide signal S769 about a gas in cuvette 764, all similarly to what was described above. In addition, capnography module 760 includes a processing component 772.

In embodiment 710, the previously mentioned monitoring circuit includes a strain gauge 770. Strain gauge 770 is attached to side tube 762. In addition, processing component 772 includes a resistor bridge 773. Resistor bridge 773 is made of resistors R1, R2, R3 as shown, and is configured to be coupled with strain gauge 770 via wires 771. In embodiment 710, processing component 772 can be configured to generate a pressure signal S779 responsive to signals on resistor bridge 773.

Figure 8:
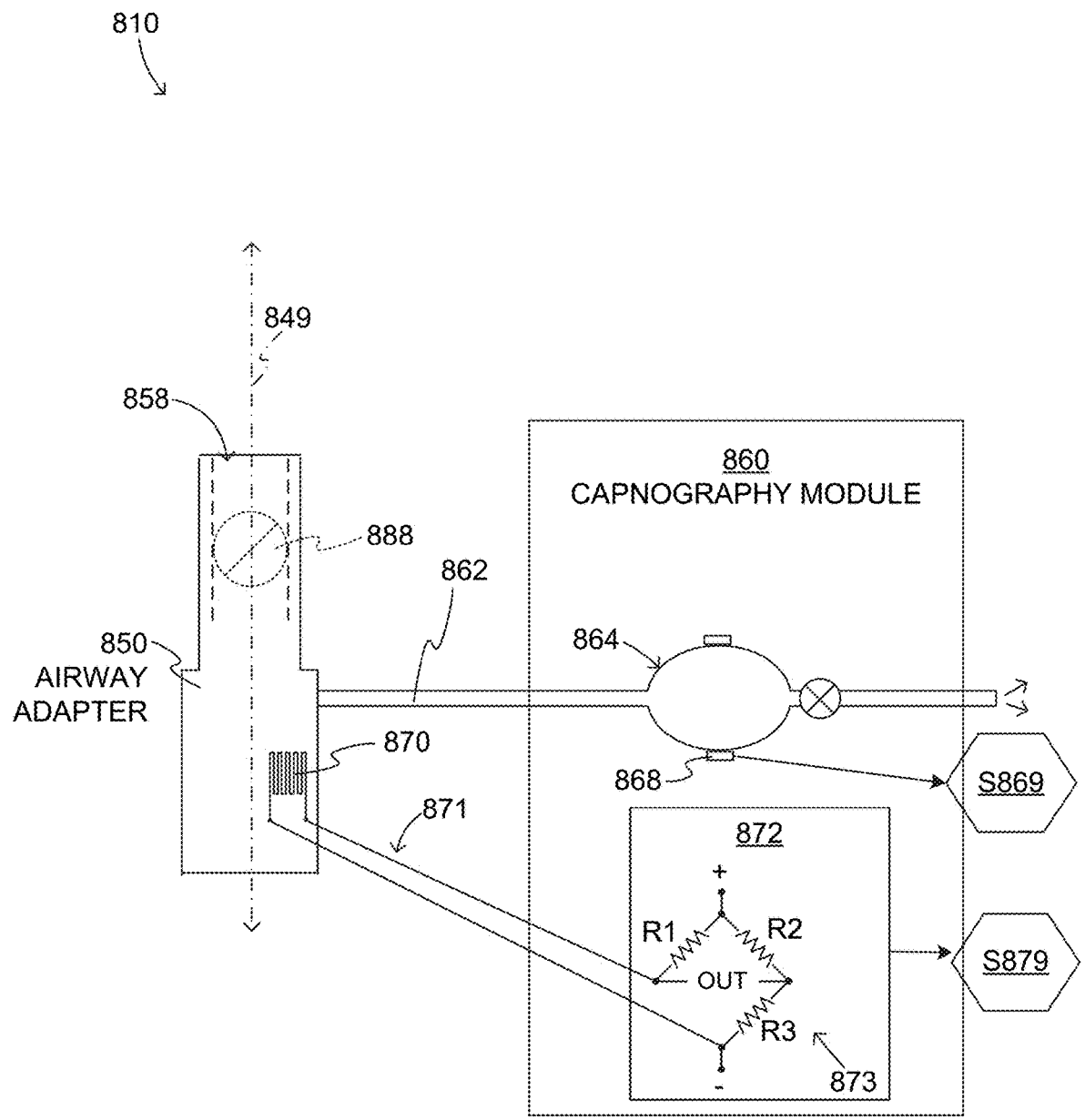
FIG. 8 is a diagram of sample embodiments of an airway adapter used together with a strain gauge and a capnography module.

For another example, referring now to FIG. 8, in an embodiment 810 an airway adapter 850 has a hollow interior 858 for accommodating an air path 849. A CPR inflow valve 888 can optionally be provided within interior 858 of airway adapter 850. Airway adapter 850 can communicate with a capnography module 860 via a side tube 862. Capnography module 860 includes a cuvette 864. Moreover, a carbon dioxide detector 868 can generate a carbon dioxide signal S869 about a gas in cuvette 864, all similarly to what was described above. In addition, capnography module 860 includes a processing component 872.

In embodiment 810, the previously mentioned monitoring circuit includes a strain gauge 870. Strain gauge 870 is attached to airway adapter 850. In addition, processing component 872 includes a resistor bridge 873. Resistor bridge 873 is made of resistors R1, R2, R3 as shown, and is configured to be coupled with strain gauge 870 via wires 871. In embodiment 810, processing component 872 can be configured to generate a pressure signal S879 responsive to signals on resistor bridge 873.

Strain gauges can be thus supported on various components according to embodiments. Such components can be, as seen above, a side tube, an airway adapter or coupler, an airway tube, a CPR inflow valve, and so on.

In some embodiments, a component on which the strain gauge is supported has proper elasticity at least at the supporting portion, for the strain gauge to give good results. In some embodiments where less overall elasticity is structurally preferable otherwise, a component may include a main portion with a first elasticity and a detection portion with a second elasticity different from the first elasticity. In such embodiments, at least a portion of the strain gauge is coupled to the detection portion. Usually the elasticity of the portion that supports the strain gauge is larger, for the strain gauge to give good results. Examples are now described.

Figure 9:
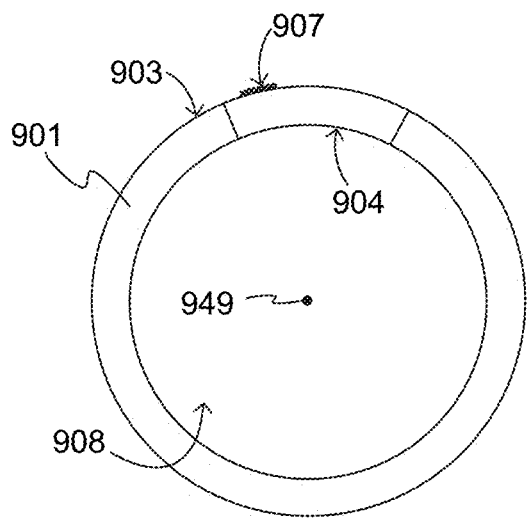
FIG. 9 is a section diagram of a component that can accommodate a strain gauge by having portions of different elasticities according to embodiments.

Referring now to FIG. 9, a section of a component 901 is shown. Component 901 can be a component as described above, which in this case is also tubular, and circular. Component 901 has a hollow interior 908, so as to accommodate an air path 949 perpendicular to the plane of the diagram. Component 901 includes a main portion 903 with a first elasticity, and a detection portion 904 with a second elasticity different from the first elasticity. At least a portion of a strain gauge 907 is coupled to detection portion 904. In the example of FIG. 9, the entire strain gauge 907 is coupled to detection portion 904, although this need not be the case. An example is now described.

Figure 10:
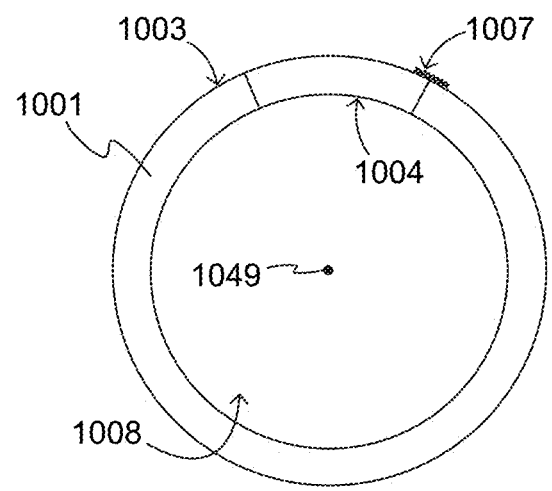
FIG. 10 is a section diagram of a component that accommodates a strain gauge on portions of different elasticities according to embodiments.

Referring now to FIG. 10, a section of a component 1001 is shown. Component 1001 can be a component as described above, which in this case is also tubular, and circular. Component 1001 has a hollow interior 1008, so as to accommodate an air path 1049 perpendicular to the plane of the diagram. Component 1001 includes a main portion 1003 with a first elasticity, and a detection portion 1004 with a second elasticity different from the first elasticity. At least a portion of a strain gauge 1007 is coupled to detection portion 1004, while at least another portion of strain gauge 1007 is coupled to main portion 1003.

The different elasticities within a single component can be accomplished in a number of ways. For example, different types of materials may be used. In some embodiments, different thicknesses are implemented, which permit using a singular material. Examples are now described.

Figure 11:
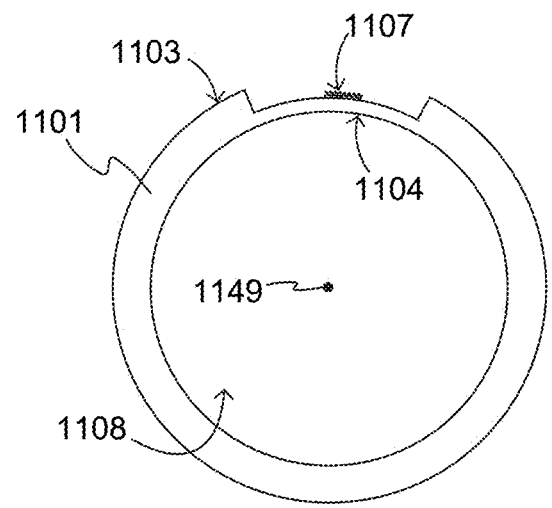
FIG. 11 is a section diagram of a component that can accommodate a strain gauge by having portions of different thicknesses according to embodiments.

Referring now to FIG. 11, a section of a component 1101 is shown. Component 1101 can be a component as described above, which in this case is also tubular, and circular. Component 1101 has a hollow interior 1108, so as to accommodate an air path 1149 perpendicular to the plane of the diagram. Component 1101 includes a main portion 1103 with a first thickness, and a detection portion 1104 with a second thickness less than the first thickness. At least a portion of a strain gauge 1107 is coupled to detection portion 1104. In other words, a section of the wall of a tube can be thinner than the ordinary tube, and embed the strain gauge in that section. As such, the amount of strain resulting from a positive pressure breath may be larger in that thinner-walled area, and easier to sense. This thinner walled section could be a longitudinal stripe in the tube, making up between 10% and 90% of the circumference of the tube.

In the example of FIG. 11, the entire strain gauge 1107 is coupled to detection portion 1104, although this need not be the case. An example is now described.

Figure 12:
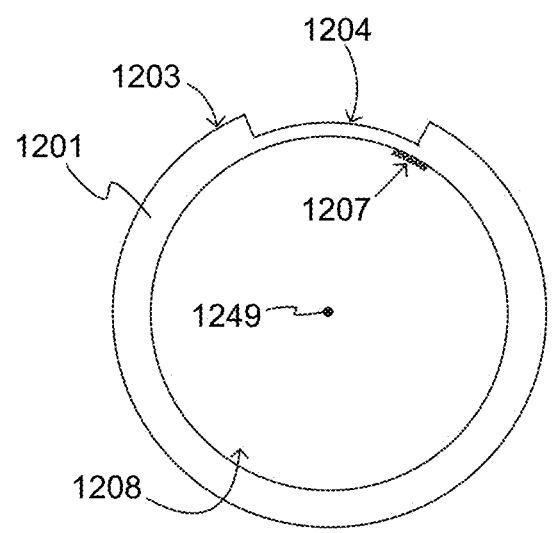
FIG. 12 is a section diagram of a component that accommodates a strain gauge on portions of different thicknesses according to embodiments.

Referring now to FIG. 12, a section of a component 1201 is shown. Component 1201 can be a component as described above, which in this case is also tubular, and circular. Component 1201 has a hollow interior 1208, so as to accommodate an air path 1249 perpendicular to the plane of the diagram. Component 1201 includes a main portion 1203 with a first thickness, and a detection portion 1204 with a second thickness less than the first thickness. At least a portion of a strain gauge 1207 is coupled to detection portion 1204, while at least another portion of strain gauge 1207 is coupled to main portion 1203.

Figure 13:
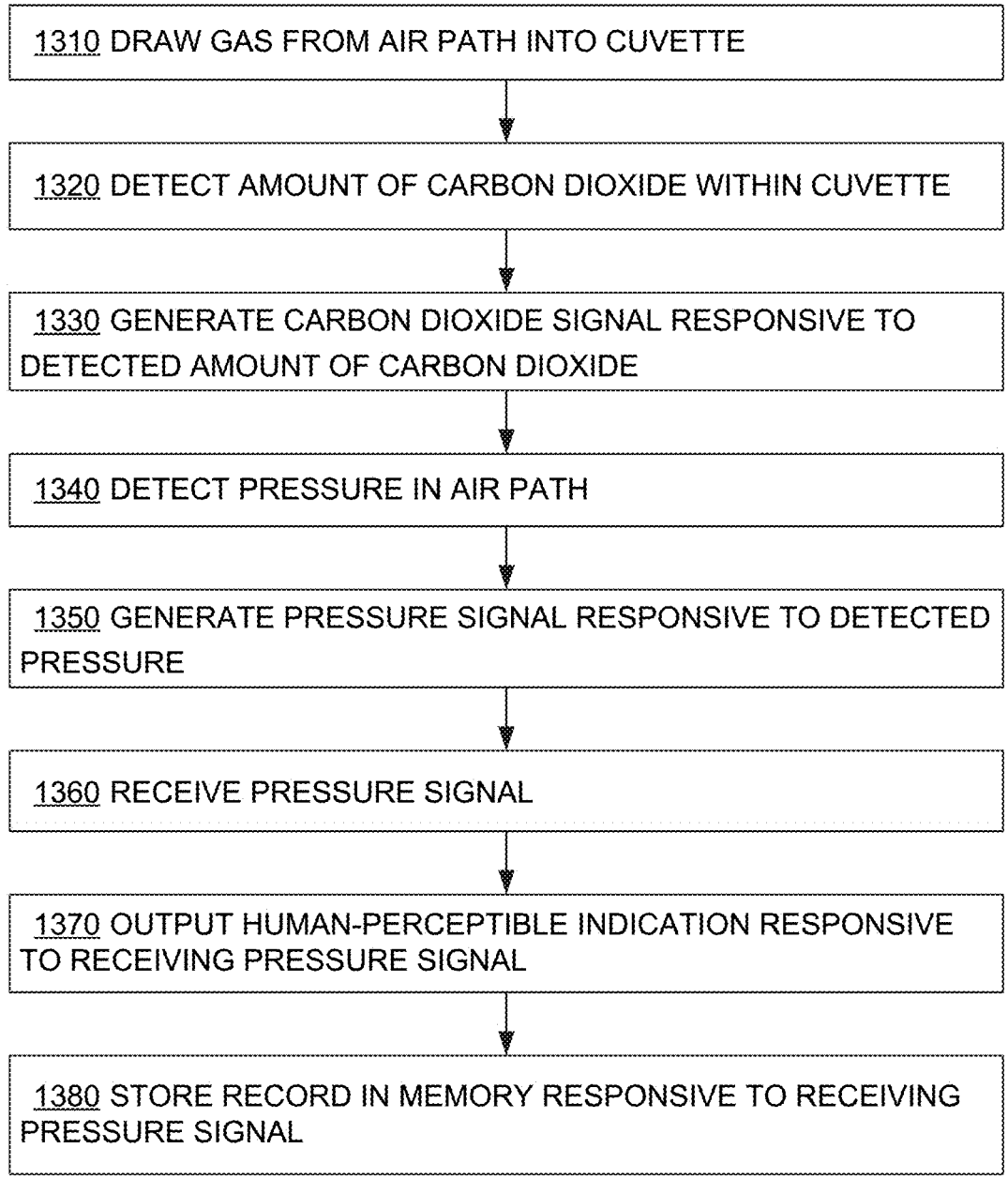
FIG. 13 is a flowchart for illustrating methods according to embodiments.

FIG. 13 shows a flowchart 1300 for describing methods according to embodiments. According to an operation 1310, gas may be drawn from an air path into a cuvette. The gas may be drawn by a pump.

According to another operation 1320, an amount of carbon dioxide within the cuvette may be detected. Detecting can be by a carbon dioxide detector.

According to another operation 1330, a carbon dioxide signal may be generated. Generating can be responsive to the amount of carbon dioxide detected at operation 1320.

According to another operation 1340, a pressure in the air path may be detected. In some embodiments, the pump is driven by a pump driving signal, a monitoring circuit includes a driving sensor, and the pressure is detected by the driving sensor detecting changes in the pump driving signal.

According to another operation 1350, a pressure signal may be generated responsive to the pressure in the air path detected at operation 1340. Generating may be performed by a processing component.

According to another operation 1360, the pressure signal generated at operation 1350 may be received by a processor.

According to another operation 1370, a human-perceptible indication may be output, responsive to the receiving at operation 1360. Outputting may be performed by an output device.

According to another operation 1380, a record may be stored in a memory responsive to the receiving at operation 1360.

Embodiments further include stand-alone versions of devices described above, which can be disposable and inexpensive. These include versions of a capnograph airway adapter, an impedance threshold device. Additional versions are now described.

Figure 14:
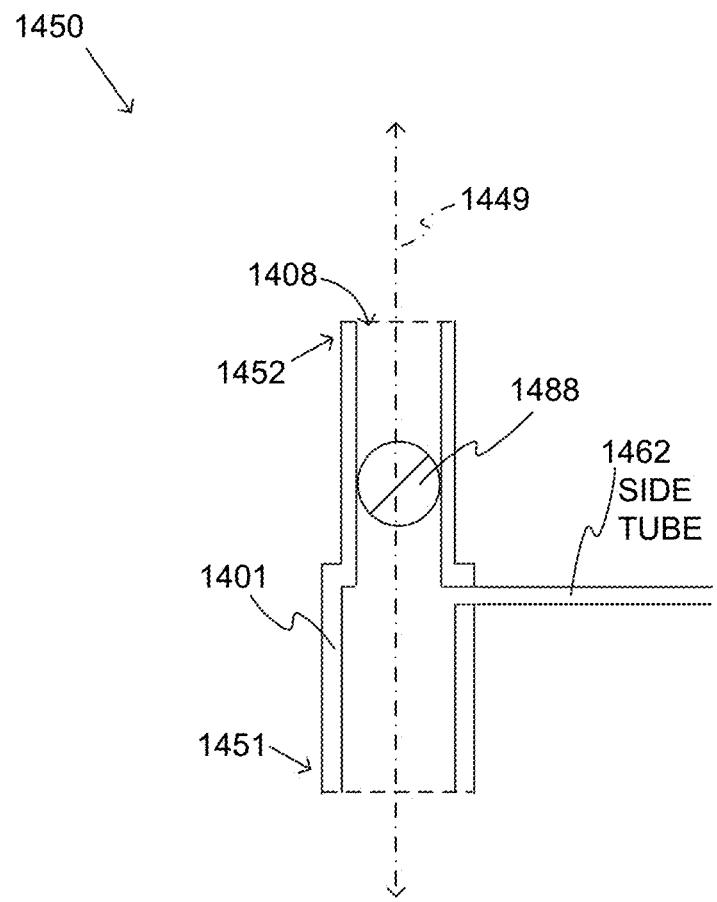
FIG. 14 is a diagram of a sample combination airway adapter with impedance threshold device, made according to embodiments.

FIG. 14 is a diagram of a sample combination device 1450 made according to embodiments, which combines an airway adapter with an impedance threshold device. Device 1450 can be an impedance threshold device configured to be used together with a ventilation system, at least as described above.

Device 1450 may include a tube section 1401, which has a first end 1451 and a second end 1452. Tube section 1401 may be made from plastic or other suitable material. Tube section 1401 may have a hollow interior 1408 for accommodating an air path 1449, when coupled between a gas source and an airway tube. Device 1450 may also include a side tube 1462 coupled to tube section 1401 and communicating with hollow interior 1408. Device 1450 may further include an inflow valve 1488 within tube section 1401, and within air path 1449, and working as described above.

Figure 15:
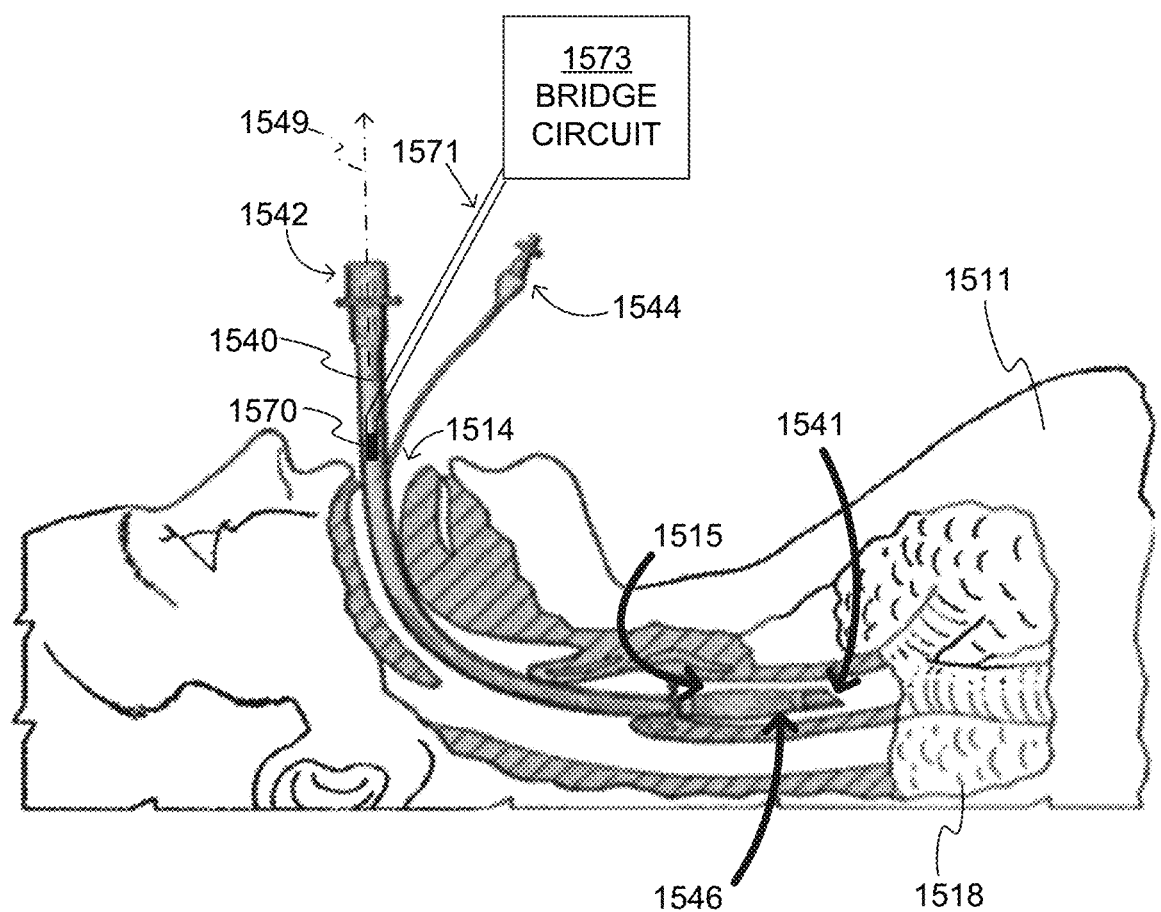
FIG. 15 is a diagram of components of a sample endotracheal (ET) system made according to embodiments, shown inserted in a patient's airway.

FIG. 15 is a diagram of a sample endotracheal (ET) system for a ventilator. The ET system includes an ET tube 1540, which has two ends 1541 and 1542. End 1542 is configured to be coupled to a gas source, which is not shown but can be made as described above. ET tube 1540 is hollow to define or accommodate an air path 1549 that receives bursts of gas expelled from a gas source, when ET tube 1540 is thus coupled with the gas source.

End 1541 is inserted in an airway of a patient 1511 having a lung 1518. Insertion is through the mouth 1514 and into trachea 1515 of patient 1511. A small syringe 1544 may be used to inflate a cuff 1546 around a portion of ET tube 1546, for forming an airtight seal between the outside of ET tube 1540 and air path 1549.

The ET system also includes a strain gauge 1570. Strain gauge 1570 is coupled to ET tube 1540, and preferably attached to it. Strain gauge 1570 can change properties when ET tube 1540 changes dimension.

The ET system further includes a bridge circuit 1573. Bridge circuit 1573 can be configured to be coupled electrically with strain gauge 1570, for example via conductors 1571. In some embodiments, bridge circuit 1573 is also physically coupled with ET tube 1540, and conductors 1571 can be very short. In other embodiments, bridge circuit 1573 is part of a module or a monitor, for example as described above. Bridge circuit 1573 can be used to generate a pressure signal about a pressure in ET tube 1540, which can help detect spontaneous breaths as per the above.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed:

1. A capnograph system configured to be used together with a ventilation system, the ventilation system including a gas source configured to expel repeated bursts of gas and an airway tube defining an air path that communicates with the gas source, the airway tube configured to be inserted in an airway of a patient so as to guide the bursts of gas as artificial inhalations to a lung of the patient, the capnograph system configured to detect carbon dioxide in exhalations of the patient and also a pressure in the air path, the capnograph system comprising:
   a capnography module having a carbon dioxide detector configured to detect a concentration of carbon dioxide within the air path and to generate a carbon dioxide signal responsive to the detected concentration of carbon dioxide in exhalations of the patient;
   a monitoring circuit distinct from the carbon dioxide detector, the monitoring circuit configured to detect a pressure in the air path, the monitoring circuit having a processing component within the capnography module that is distinct from the carbon dioxide detector, the processing component generating a pressure signal responsive to the pressure detected in the air path by the monitoring circuit; and
   a processor configured to combine the carbon dioxide signal and the pressure signal into a combined signal by removing peaks in the carbon dioxide signal that correspond to peaks in the pressure signal and to detect spontaneous breaths of the patient based at least in part on peaks in the combined signal.

2. The capnograph system of claim 1, wherein
   the monitoring circuit is wholly included within the capnography module.

3. The capnograph system of claim 1, wherein
   the pressure signal alone is used to detect spontaneous breaths of the patient.

4. The capnograph system of claim 1, further comprising:
   an output device configured to output a human-perceptible indication responsive to the processor receiving the pressure signal.

5. The capnograph system of claim 4, further comprising:
   a monitor that includes the capnography module, the processor and the output device.

6. The capnograph system of claim 4, further comprising:
   a defibrillator; and
   a monitor that includes the capnography module, the processor and the output device.

7. The capnograph system of claim 1, further comprising:
   a memory configured to store a record responsive to the processor receiving the pressure signal.

8. The capnograph system of claim 7, further comprising:
   a monitor that includes the capnography module, the processor and the memory.

9. The capnograph system of claim 7, further comprising:
   a defibrillator; and
   a monitor that includes the capnography module, the processor and the memory.

10. The capnograph system of claim 1, wherein
    the capnography module includes:
    a cuvette configured to communicate with the air path;
    a pump configured to draw gas from the air path into the cuvette,
    and an exhaust tube from which sampled gases can be disposed from the air path;
    the carbon dioxide detector is configured to detect a concentration of carbon dioxide within the cuvette, and
    the monitoring circuit includes a pressure sensor configured to detect a pressure of the gas within the cuvette.

11. The capnograph system of claim 1, wherein
    the capnography module includes:
    a cuvette configured to communicate with the air path; and
    a pump configured to draw gas from the air path into the cuvette, the pump having a power node, the pump configured to receive a pump driving signal at the power node, and to operate responsive to the pump driving signal,
    the carbon dioxide detector is configured to detect a concentration of carbon dioxide within the cuvette, and
    the monitoring circuit includes a driving sensor configured to detect changes in the pump driving signal.

12. The capnograph system of claim 11, further comprising:
    an airway adapter configured to be coupled between the gas source and the airway tube, the airway adapter having a hollow interior so as to accommodate the air path when the airway adapter is thus coupled;

a side tube configured to be coupled between the airway adapter and the cuvette, and in which the monitoring circuit includes a pressure detector coupled to the airway adapter and configured to detect a pressure in the hollow interior, the pressure detector configured to generate a pressure detection signal responsive to the pressure detected in the hollow interior, the monitoring circuit further includes an antenna configured to transmit wirelessly the pressure detection signal, the capnography module further includes a wireless communication module (WCM) configured to receive the wirelessly transmitted pressure detection signal and to convey an interim signal to the processing component responsive to the received pressure detection signal, and the processing component is configured to generate the pressure signal responsive to the received interim signal.

13. The capnograph system of claim 12, further comprising:

an inflow valve within the interior of the airway adapter, the inflow valve configured to be closed so as to block the air path and thus prevent the bursts of gas from entering the lung until a negative airway pressure threshold is exceeded, at which time the closed inflow valve is configured to open so as to unblock the blocked air path.

14. The capnograph system of claim 1, further comprising:

an airway adapter configured to be coupled between the gas source and the airway tube, the airway adapter having a hollow interior so as to accommodate the air path when the airway adapter is thus coupled; and a side tube configured to be coupled between the airway adapter and the cuvette, and in which the monitoring circuit includes a strain gauge.

15. The capnograph system of claim 14, further comprising:

an inflow valve within the interior of the airway adapter, the inflow valve configured to be closed so as to block the air path and thus prevent the bursts of gas from entering the lung until a negative airway pressure threshold is exceeded, at which time the closed inflow valve is configured to open so as to unblock the blocked air path.

16. The capnograph system of claim 14, wherein the monitoring circuit further includes a bridge circuit configured to be coupled with the strain gauge.

17. The capnograph system of claim 16, wherein the bridge circuit is not within the capnography module.

18. The capnograph system of claim 16, wherein the bridge circuit is within the capnography module.

19. The capnograph system of claim 14, wherein the strain gauge is attached to the side tube.

20. The capnograph system of claim 14, wherein the strain gauge is attached to the airway adapter.

21. The capnograph system of claim 20, wherein the airway adapter includes a main portion with a first elasticity and a detection portion with a second elasticity different from the first elasticity, and at least a portion of the strain gauge is coupled to the detection portion.

22. The capnograph system of claim 21, wherein at least another portion of the strain gauge is coupled to the main portion.

23. The capnograph system of claim 21, wherein the main portion has a first thickness, and the detection portion has a second thickness less than the first thickness.

24. A method for a capnograph system that is configured to be used together with a ventilation system, the ventilation system including a gas source expelling repeated bursts of gas and an airway tube defining an air path that communicates with the gas source, the airway tube inserted in an airway of a patient and guiding the bursts of gas as artificial inhalations to a lung of the patient, the capnograph system including a capnography module and a monitoring circuit, the monitoring circuit having a processing component within the capnography module, the capnography module comprising a cuvette communicating with the air path, a pump, and a carbon dioxide detector distinct from the monitoring circuit and from the processing component, the method comprising:

drawing, by the pump, gas from the air path into the cuvette at a constant rate;

detecting, by the carbon dioxide detector, a concentration of carbon dioxide within the cuvette and generating a carbon dioxide signal responsive thereto;

detecting a pressure in the air path;

generating, by the processing component, a pressure signal responsive to the detected pressure in the air path;

combining the carbon dioxide signal and the pressure signal into a combined signal by removing peaks in the carbon dioxide signal that correspond to peaks in the pressure signal; and detecting a spontaneous breath of the patient based at least in part on the combined signal.

25. The method of claim 24, wherein the pressure signal alone is used to detect spontaneous breaths of the patient.

26. The method of claim 24, wherein the capnograph system further includes: a processor and an output device, and the method further comprises:

receiving, by the processor, the pressure signal; and outputting, by the output device, a human-perceptible indication responsive to the processor receiving the pressure signal.

27. The method of claim 24, wherein the capnograph system further includes: a processor and a memory, and the method further comprises:

receiving, by the processor, the pressure signal; and storing in the memory a record responsive to the processor receiving the pressure signal.

28. The method of claim 24, wherein the pump is driven by a pump driving signal, the monitoring circuit includes a driving sensor, and the pressure is detected by the driving sensor detecting changes in the pump driving signal.

* * * * *